(12) United States Patent
Mok

(10) Patent No.: US 7,314,867 B2
(45) Date of Patent: Jan. 1, 2008

(54) PHARMACEUTICAL COMPOSITION COMPRISING A RETRO-IVERSO ISOMER PEPTIDE

(76) Inventor: Kenneth Hun Mok, 1 Varsity Place, John Towle Close, Oxford, Oxfordshire OX1 4TY (GB)

( * ) Notice: Subject to any disclaimer, the term of this patent is extended or adjusted under 35 U.S.C. 154(b) by 0 days.

(21) Appl. No.: 10/517,355

(22) PCT Filed: May 23, 2003

(86) PCT No.: PCT/KR03/01017

§ 371 (c)(1),
(2), (4) Date: Nov. 22, 2004

(87) PCT Pub. No.: WO03/099315

PCT Pub. Date: Dec. 4, 2003

(65) Prior Publication Data

US 2005/0261199 A1    Nov. 24, 2005

(30) Foreign Application Priority Data

May 23, 2002  (GB) ................................ 0211849.5

(51) Int. Cl.
*A61K 5/08* (2006.01)
(52) U.S. Cl. ........................................ 514/18; 530/331
(58) Field of Classification Search .................. 514/18; 530/331
See application file for complete search history.

(56) References Cited

U.S. PATENT DOCUMENTS

| | | | |
|---|---|---|---|
| 4,473,555 A * | 9/1984 | Nestor et al. .................. | 514/15 |
| 5,218,089 A | 6/1993 | Mariotti et al. .............. | 530/333 |
| 5,451,658 A * | 9/1995 | Seelig ......................... | 530/300 |
| 5,723,443 A | 3/1998 | Kagawa et al. | |
| 5,756,467 A | 5/1998 | Kagawa et al. | |
| 5,831,003 A * | 11/1998 | Baumbach et al. ......... | 530/329 |
| 5,958,885 A | 9/1999 | Kagawa et al. | |
| 6,046,168 A | 4/2000 | Kagawa et al. | |
| 2005/0049193 A1 * | 3/2005 | Grasso et al. ................ | 514/12 |

FOREIGN PATENT DOCUMENTS

| | | |
|---|---|---|
| EP | 0 253 190 A2 | 1/1988 |
| EP | 0 253 190 A3 | 1/1988 |
| EP | 0 838 473 B | 10/2002 |

OTHER PUBLICATIONS

Abstract of JP 11-263733 (Sep. 1999).*
Abstract of WO 97/00890 (Jan. 1997).*
Abstract of WO 89/06970 (Aug. 1989).*
Josef R. Patsch, et al., Relation of Triglyceride Metabolism and Coronary Artery Disease, Arteriosclerosis and Thrombosis, 199, 12:1336-1345.
Michael Chorev, et al., A Dozen Years of Retro-Inverso Peptidomimetics, Acc, Chem. Res, 1993, 26, 266-274.
Michael Choev, et al. Recent Developments In Retro Peptides And Proteins—An Ongoing Topochemical Exploration, Tibtech, Oct. 1995, vol. 13, pp. 438-445.
Matthew David Fletcher, et al., Partially Modified Retro-Inverso Peptides: Development, Synthesis, and Conformational Behavior, Chem. Rev. 1998, 98, 763-795.
Melissa A. Austin, Plasma Triglyceride As A Risk Factor For Coronary Heart Disease, The Epidemiologic Evidence and Beyond, American Journal of Epidemiology, 1989, vol. 129, No. 2, pp. 249-259.
S. Muller, The Potential of Retro-Inverso Peptides as Synthetic Vaccines, Ashley Publications Ltd., 1998, ISSN 1354-3784, pp. 1429-1439.
F. Nargi, Protection of Swine from Foot-and-Mouth Disease with One Doe of an All-D Retro Peptide, Vaccine 17 (1999) 288-2893.

* cited by examiner

*Primary Examiner*—David Lukton
(74) *Attorney, Agent, or Firm*—Frommer Lawrence & Haug LLP; Ronald R. Santucci

(57) ABSTRACT

The present invention provides a pharmaceutical composition comprising a peptide selected from the group consisting of D-Pro D-Tyr D-Val D-Val, D-Pro D-Tyr D-Val, and D-Leu D-Thr D-Val as an active component. The composition of the present invention has great efficacy in lowering serum triglyceride levels.

6 Claims, 1 Drawing Sheet

I

II

PHARMACEUTICAL COMPOSITION COMPRISING A RETRO-IVERSO ISOMER PEPTIDE

This application is a 371 of PCT/KR03/01017 filed on May 23, 2003, published on Dec. 4, 2003 under publication number WO 03/099315 A1 which claims priority benefits from Great Britain patent application number GB 0211849.5 filed May 23, 2002.

BACKGROUND OF THE INVENTION

1. Field of the Invention

The present invention relates to therapeutic peptides that possess inhibitory activity towards elevation of serum triglyceride (triacylglycerol) levels, an unavoidable result that occurs upon ingestion of meals containing high composition of fat. Administration of such peptides before or concomitantly with meals allows for less net absorption of fatty acids into the system, thereby contributing to the prevention of various known cardiovascular diseases as well as obesity-related ailments in general.

2. Description of the Related Art

High serum triglyceride level, independent of the well-known risk factor of serum cholesterol, has been regarded as an additional risk factor for developing cardiovascular diseases, including coronary heart disease (Austin M A, *Am. J. epidemiol.* 129: 249-59, 1989) and atherosclerosis (Patsch J R et al, *Arterioscler. Thromb.* 12: 1336-45, 1992). A number of pharmaceutical developments have been made to restrict the elevation of serum triglyceride levels to prevent such cardiovascular ailments.

More significantly, the excessive intake of lipid with respect to energy expenditure leads to obesity, which is currently being regarded as one of the prime health concerns in the Western World. Obesity is a complex medical disorder with implications for diabetes, high cholesterol, cardiovascular conditions, some forms of cancer, and is a major cause of premature mortality. Dietary restriction and behavioral changes are key to prevent obesity, however it is now becoming evident that the success in preventing or treating obesity can be increased with pharmaco-therapy. Several drugs have been developed to combat obesity, however most of these are central-nervous system (CNS)-active, and hence have high abuse potential. Therefore, it would be desirable to have a pharmaceutical agent that would not have these dependency complications.

Recently, a group of low molecular weight peptides which were originally obtained and purified from a non-specific enzymatic proteolysate preparation of bovine reticulocyte protein has been shown to inhibit the elevation of serum triglyceride levels (U.S. Pat. No. 5,958,885). The peptides isolated are low molecular weight, i.e. 3-4 residues in length, and are comprised solely of natural amino acids.

Now, retro-inverso technology, in which oligopeptides are synthesised that are similar to naturally occurring oligopeptides but with mirror image amino acids put in reverse sequence order (Chorev M, Goodman M, TIBTECH 13:438-45, 1995), is a technology that has had limited take-up in recent years. By utilizing non-natural D-amino acids instead of L-amino acids, it can provide an advantage in bioavailability due to inherent resistance against various natural proteases in vivo but there is no expectation for its use to effectively mimic or better the biological action of naturally occurring peptides.

SUMMARY OF THE INVENTION

The present invention provides a pharmaceutical composition or a food composition for administration to a human or an animal comprising a retro-inverso isomer peptide as an active component.

In one aspect of the present invention there is provided a pharmaceutical composition for administration to a human or an animal comprising, as an active component, a peptide selected from the group consisting of D-Pro D-Tyr D-Val D-Val, D-Pro D-Tyr D-Val, and D-Leu D-Thr D-Val.

These peptides have unexpectedly been found to have a biological activity to reduce serum triglycerides. Among them, the peptides of D-Pro D-Tyr D-Val and D-Leu D-Thr D-Val substantially exceed the activity of the corresponding natural oligopeptide.

Unlike the natural oligopeptides, the peptides obtained from the retro-inverso chemical synthesis process are also available for functional group modifications, if required. This modification further allows for greater specificity and selectivity, and will also permit to tailor the activities of the peptides to suit the patient based on his/her intake of fat composition.

The peptide may, within the scope of the claimed invention, have minor modifications of a nature that is compatible with biological systems, suitably including phosphorylation, sulphonation or iodination of the D-Tyr and/or D-Thr. The D-Pro may, for example, be hydroxylated. Widely used automatic solid-phase peptide synthetic methods for performing the modification include N-alpha-acetylation or N-alpha-formylation for eliminating the positive charge of the N-terminus. When desiring to eliminate the negative charge on the C-terminus, a C-terminal carboxamide or alcohol ester can be readily generated by adopting standard solid-phase peptide synthetic resins.

For optimal activity, the peptide may be modified at the N or C, and suitably both, terminals of the peptide.

Complete reversal of ionization state can also be straightforwardly performed. The N-terminal $NH_2$ group is suitably replaced with a COOH group and the C-terminal COOH group is suitably replaced with an $NH_2$ group. This modification may suitably be undertaken using one of the conventional techniques for this purpose.

A route for this modification involves:

(1) a C-2 substituted malonyl (or malonamyl) residue substitution for the N-terminal retro-inverso peptide residue, and (2) a gem-diamino alkyl residue substitution for the C-terminal retro-inverso peptide residue.

The pharmaceutical composition is suitably provided in a form selected from the group consisting of a tablet, a powder, a granule, a pill and an injectable form. If provided in an injectable form it is suitably selected from the group consisting of a solution, a suspension and an emulsion.

The said injectable form may be administered by intravenous, intramuscular, subcutaneous, intracutaneous and intraperitoneal administration. The pharmaceutical composition suitably comprises from 1 to 100 mg of said peptide.

According to a second aspect of the invention there is suitably provided a food composition for administration to a human or an animal comprising a peptide consisting of D-Pro D-Tyr D-Val D-Val, D-Pro D-Tyr D-Val, and D-Leu D-Thr D-Val as an active component.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Figure 1:
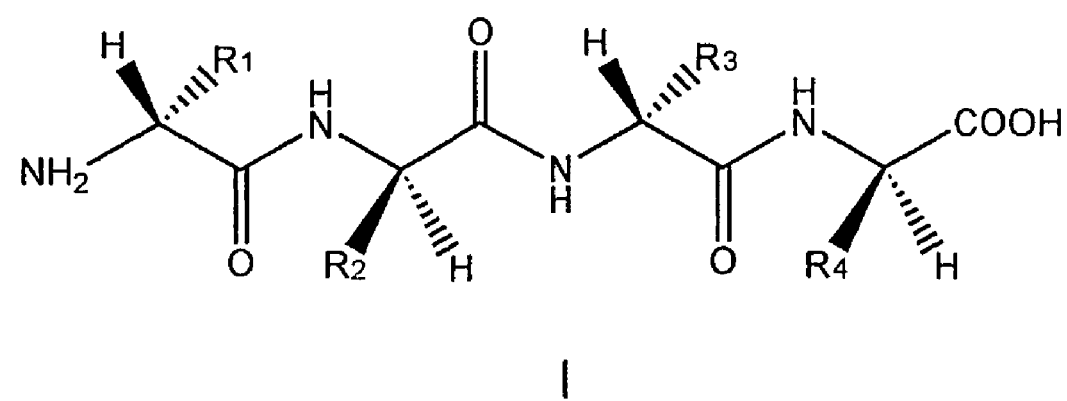
FIG. 1 shows the structural differences between the retro-inverso peptide H—$_D$—$R_1$—$_D$—$R_2$—$_D$—$R_3$—$_D$—$R_4$—OH (Structure 1) and the end-group modified peptide HO-m$R_1$—$_D$—$R_2$—$_D$—$R_3$-g$R_4$—H (Structure II, where m and g denote malonyl and gem-diaminoalkyl residues, respectively).
Figure 1:
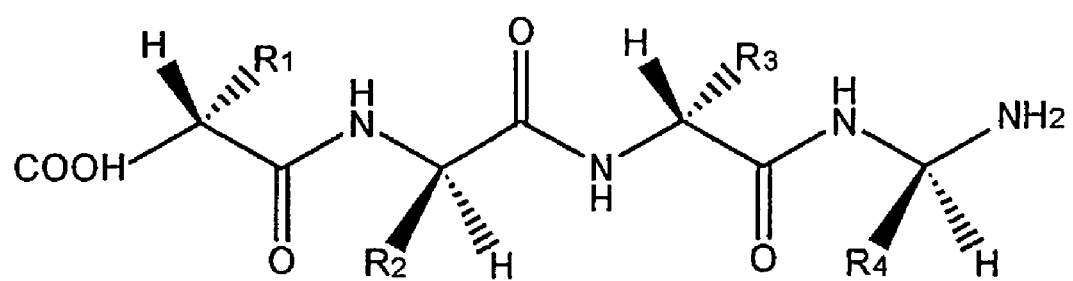

The present invention is further illustrated and described by the following examples, which should not be taken to limit the scope of the invention.

EXAMPLE 1

Chemical Synthesis and Purification of Peptides

Peptides of D-Pro D-Tyr D-Val D-Val, D-Pro D-Tyr D-Val and D-Leu D-Thr D-Val were synthesized on an Applied Biosystems/Perkin-Elmer 432A Synergy Peptide Synthesizer using FastMoc cycles. The synthesis chemistry involves 2-(1H-benzotriazol-1-yl)-1,1,3,3-tetramethyluronium hexafluorophosphate (HBTU)/piperidine activation, and uses dimethylformamide (DMF)/N-methylpyrrolidine (NMP)/dimethylsulfoxide (DMSO) as the coupling solvent. Synergy Fmoc-Amide resin (Applied Biosystems/Perkin-Elmer) or Rink amide methylbenzhydrylamine (MBHA) resin (NOVAbiochem) was used for the solid-phase support. The constituting N-α-9-fluorenylmethoxycarbonyl (Fmoc) protected D-amino acids (N-α-Fmoc-D-proline, N-α-Fmoc-O-t-butyl-D-tyrosine, N-α-Fmoc-D-valine, N-α-Fmoc-D-leucine, N-α-Fmoc-O-t-butyl-D-threonine) were from NOVABIOCHEM. The peptides were cleaved by adding 1.8 ml of trifluoroacetic acid (TFA) with 0.1 ml of 1,2-ethanedithiol (EDT) and 0.1 ml of thioanisole as scavengers for 1 hour, then precipitated with 15 ml of methyl tert-butyl ether (MTBE) at 4° C. and centrifugation at 2000×g. The MTBE washing was repeated three more times, and the peptides were solubilized with 20% acetic acid. To use as reference compounds, L-Val-L-Val-L-Tyr-L-Pro, L-Val-L-Tyr-L-Pro, and L-Val-L-Thr-L-Leu peptides were prepared using the same methodology.

When necessary, purification of the peptides was performed using preparative reversed-phase HPLC. A Kromasil KR-100-10-C8 (10 mm×250 mm, C8, 10 μm, 100 A, Akzo Nobel) Column was used, with a linear gradient of 5 to 20% acetonitrile ($CH_3CN$) in 0.1% TFA over 20 column volumes. The fractionated peak was checked for purity using a Vydac (Registered Trade Mark) 218TP52 RP-HPLC column (2.1 mm×250 mm, C8, 5 μm, 300 A) with a linear gradient of 1 to 25% $CH_3CN$ in 0.1% TFA. The final purity of each peptide was greater than 97%. MALDI-TOF mass spectrometry analyses using cinnapinic acid as matrix on a Kompact Research MALDI IV instrument (Kratos Analytical) confirmed the identities of the peptides.

EXAMPLE 2

Oral Administration of Chemically Synthesised Peptides to Determine Inhibition of Triglyceride Level Elevation After Feeding Olive oil (250 mg) was administered via gastric intubation to male ICR mice (6-week old, body weight: 20 g), which were fasted overnight. The peptides were dissolved in 0.1 ml saline solution and administered orally one hour after lipid administration. For the control group, 0.1 ml of saline solution was administered per mouse. After two hours, blood was collected from the orbital vein under ether anesthesia and the serum was separated by centrifugation (3000 rpm, 30 min, 1° C.). Serum triglyceride levels were assayed using commercially available methods (e.g. INFINITY (Registered Trade Mark) triglycerides reagent; Sigma Chemical Co.). The results were compared with L-Val-L-Val-L-Tyr-L-Pro (Reference Peptide 1), L-Val-L-Tyr-L-Pro (Reference Peptide 2), and L-Val-L-Thr-L-Leu (Reference Peptide 3) and shown in Table 1.

TABLE 1

|  | Peptide Dosage (mg/mouse) | Number of animal (n) | Serum Triglyceride (mg/100 ml) | % Decrease |
|---|---|---|---|---|
| Distilled Water Only | — | 5 | 92.2 ± 15.7 | — |
| Olive Oil Only | — | 24 | 376.2 ± 23.8 | — |
| Retro Inverso Polypeptide 1 (D-Pro D-Tyr D-Val D-Val C-$NH_2$) | 1.0 | 14 | 313.7 ± 45.9 | 22.0% |
| Ref. Peptide 1 (L-Val L-Val L-Tyr L-Pro) | 1.0 | 7 | 244.7 ± 25.5 | 46.3% |
| Retro Inverso Polypeptide 2 (D-Pro D-Tyr D-Val C-$NH_2$) | 1.0 | 7 | 231.8 ± 27.6 | 50.8% |
| Ref. Peptide 2 (L-Val L-Tyr L-Pro) | 1.0 | 14 | 407.7 ± 42.0 | 0% |
| Retro Inverso Polypeptide 3 (D-Leu D-Thr D-Val C-$NH_2$) | 1.0 | 7 | 294.6 ± 33.8 | 28.7% |
| Ref. Peptide 3 (L-Val L-Thr L-Leu) | 1.0 | 14 | 352.7 ± 35.6 | 8.3% |

In Table 1, "C—$NH_2$" means that the C-terminal of a peptide has a carboxamide form.

As shown in Table 1, Retro Inverso Polypeptide 1 and Retro Inverso Polypeptide 3 display higher activities in lowering elevated serum triglyceride levels than Reference 2 and 3, respectively. Retro Inverso Polypeptide 1, although less active than Reference Peptide 1, nevertheless exhibits demonstrable serum triglyceride lowering activity, its activity being about half of Reference Peptide 1. In general, it can be shown that for the three cases, there exist at least 20% or greater statistically significant decrease in serum triglyceride levels, and for the cases of tripeptides, the retro-inverso compounds substantially exceed the activity of the corresponding natural oligo-peptides.

As noted previously, for enhanced efficacy the retro-inverso peptides suitably have modified N and C terminals, where the N-terminal of the retro-inverso peptide is converted to replace the $NH_2$ group with a COOH group and the C-terminal COOH group is replaced with an $NH_2$ group. This modification may be achieved by carrying out a C-2 substituted malonyl (or malonamyl) residue substitution for the N-terminal retro-inverso peptide residue (Residue $R_1$ in FIG. 1), and a gem-diamino alkyl residue substitution for the C-terminal retro-inverso is peptide residue (Residue $R_4$).

FIG. 1 shows the structural differences between the retro-inverso peptide H—$_D$—$R_1$—$_D$—$R_2$—$_D$—$R_3$—$_D$—$R_4$—OH (Structure 1) and the end-group modified peptide HO-mR$_1$—$_D$—R$_2$—$_D$—R$_3$-gR$_4$—H (Structure II, where m and g denote malonyl and gem-diaminoalkyl residues, respectively).

Procedures to accomplish these end group modifications are well-documented, and are reviewed in Fletcher M D, Campbell M M, Chem Rev 1998, 98: 763-795 and Chorev M, Goodman, Acc Chem Res 1993, 26:266-73.

According to the present invention, it becomes possible to prevent hyperlipemia in human and domestic animals upon administration of the peptides found in the sequence listing. Such treatment is now known to have far reaching benefits, including but not restricted to, cardiovascular ailments such as hypertension and arteriosclerosis, and obesity-related complications in general.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pharmaceutical composition comprising a pharmaceutically acceptable carrier and a peptide, wherein the peptide is selected from the group consisting of D-Pro D-Tyr D-Val and D-Leu D-Thr D-Val, and wherein
    the C-terminal COOH group of the peptide is amidated.
2. The pharmaceutical composition of claim 1, being selected from the group consisting of a tablet, a powder, a granule, a pill and an injectable form.
3. The pharmaceutical composition of claim 2, which is an injectable form.
4. The pharmaceutical composition of claim 3, wherein said injectable form is selected from the group consisting of a solution, a suspension and an emulsion.
5. The pharmaceutical composition of claim 1, wherein the composition comprises from 1 to 100 mg of said peptide.
6. A food composition comprising a peptide, wherein the peptide is selected from the group consisting of D-Pro D-Tyr D-Val and D-Leu D-Thr D-Val, and wherein
    the C-terminal COOH group of the peptide is amidated.

* * * * *